US009441220B2

(12) United States Patent
Chen et al.

(10) Patent No.: US 9,441,220 B2
(45) Date of Patent: Sep. 13, 2016

(54) METHOD AND APPARATUS FOR ISOLATING NUCLEIC ACIDS

(71) Applicant: GENERAL ELECTRIC COMPANY, Schenectady, NY (US)

(72) Inventors: Lin Chen, Shanghai (CN); Bing Shang, Shanghai (CN); Klaus Hochleitner, Dassel (DE); Rong Hou, Shanghai (CN); Yanju Wang, Shanghai (CN)

(73) Assignee: General Electric Company, Schenectady, NY (US)

( * ) Notice: Subject to any disclaimer, the term of this patent is extended or adjusted under 35 U.S.C. 154(b) by 48 days.

(21) Appl. No.: 14/364,436

(22) PCT Filed: Dec. 20, 2012

(86) PCT No.: PCT/US2012/070862
§ 371 (c)(1),
(2) Date: Jun. 11, 2014

(87) PCT Pub. No.: WO2013/096575
PCT Pub. Date: Jun. 27, 2013

(65) Prior Publication Data
US 2015/0299693 A1    Oct. 22, 2015

(30) Foreign Application Priority Data
Dec. 22, 2011  (CN) .......................... 2011 1 0436344

(51) Int. Cl.
| | | |
|---|---|---|
| *C07H 21/00* | (2006.01) | |
| *C12N 15/10* | (2006.01) | |
| *B01J 20/10* | (2006.01) | |
| *B01J 20/28* | (2006.01) | |
| *B01J 20/281* | (2006.01) | |
| *C07H 1/06* | (2006.01) | |
| *C07H 1/08* | (2006.01) | |

(52) U.S. Cl.
CPC .......... *C12N 15/1017* (2013.01); *B01J 20/103* (2013.01); *B01J 20/281* (2013.01); *B01J 20/28023* (2013.01); *B01J 20/28038* (2013.01); *B01J 2220/82* (2013.01); *C07H 1/06* (2013.01); *C07H 1/08* (2013.01)

(58) Field of Classification Search
None
See application file for complete search history.

(56) References Cited

U.S. PATENT DOCUMENTS

| | | | | |
|---|---|---|---|---|
| 4,883,764 A | * | 11/1989 | Kloepfer | G01N 33/48 422/430 |
| 8,586,348 B2 | * | 11/2013 | Wang | B01L 3/502776 422/68.1 |
| 9,012,641 B2 | | 4/2015 | Tuksar et al. | |
| 2005/0079535 A1 | * | 4/2005 | Kirchgesser | C12N 15/1003 435/6.12 |
| 2005/0214926 A1 | | 9/2005 | Zielenski et al. | |
| 2008/0153078 A1 | * | 6/2008 | Braman | B01L 3/502 435/2 |
| 2008/0241953 A1 | | 10/2008 | Fish | |
| 2010/0027013 A1 | | 2/2010 | Hansen | |

FOREIGN PATENT DOCUMENTS

| | | |
|---|---|---|
| WO | 02/16383 A1 | 2/2002 |
| WO | 2010/039802 A2 | 4/2010 |
| WO | 2012/157831 A1 | 11/2012 |

OTHER PUBLICATIONS

Martin et al. Carcinogenesis (1998), vol. 19, pp. 1061-1069.*
Mao et al. Anal. Chem. (2009), vol. 81, pp. 1660-1668.*
Nanohelix Co., Ltd.: "Punch-it NA-Sample Kit, Instructions for Use," Nov. 16, 2011, retrieved from the internet URL http://www.nanohelix.net/02_products/ist.asp?cate_code=203, retrieved on Jul. 14, 2015, 4 pages.
Jangam et al., "Rapid, Point-of-Care Extraction of Human Immunodeficiency Virus Type 1 Proviral DNA from Whole Blood for Detection by Real-Time PCR," Journal of Clinical Microbiology, American Society for Microbiology, US, vol. 47, No. 8, Aug. 1, 2009, 6 pages.
Baker et al., "Isolation of Genomic DNA Filtered from Blood Using a Novel Filter-Based DNA Purification Technology," Biotechniques, Informa Healthcare, US, vol. 31, No. 1, Jul. 1, 2001, 4 pages.
PCT/US2012/070862 ISRWO Dated Mar. 14, 2013.

* cited by examiner

*Primary Examiner* — Patrick Lewis

(57) ABSTRACT

A method comprises: sorbing a sample solution comprising nucleic acids to a sample receiving portion of a quartz fiber filter by contacting the sample solution with the sample receiving portion; and washing the sample receiving portion while keeping most of nucleic acids around the sample receiving portion by flowing a wash solution through the sample receiving portion under a wicking force directed away from the sample receiving portion. An associated apparatus is also provided.

9 Claims, 7 Drawing Sheets

METHOD AND APPARATUS FOR ISOLATING NUCLEIC ACIDS

This application is a filing under 35 U.S.C. 371 of international application number PCT/US2012/070862, filed Dec. 20, 2012, which claims priority to China application number 201110436344.3 filed Dec. 22, 2011, the entire disclosure of which is hereby incorporated by reference.

BACKGROUND

The invention relates generally to methods and apparatuses for isolating nucleic acids.

Nucleic acids have a variety of usages in different areas such as detection or diagnosis area. Detection or diagnosis at the nucleic acid level is more sensitive or specific than at, e.g., the protein level. Analytes such as crude extracts from tissues like plant or animal tissue, cell lysate, or blood or urine samples comprise, besides nucleic acids, other species (or impurities) at least some of which may inhibit the nucleic acid detections or masking the detection results, so it is usually necessary to isolate nucleic acids from the impurities. Analytes comprising nucleic acids are usually available in small amounts, so amplification techniques like the polymerase chain reaction (PCR) or reverse-transcriptase-polymerase chain reaction (RT-PCR) are developed. Sometimes, one of requirements to isolation of nucleic acids would be obtaining amounts of nucleic acids from analytes enough to be used in the subsequent amplification procedures.

Different technologies have been developed to isolate/separate/purify nucleic acids. For example, U.S. patent application publication No. 2005/0112658 discloses a method of isolating and purifying a nucleic acid under a centrifugal force, U.S. patent application publication No. 2007/0221563 discloses a method for separating and purifying a nucleic acid under pressure, and international patent application publication No. 2007/104962 directs to a method for separating nucleic acids from a liquid sample by allowing the liquid sample to flow along a bibulous membrane so that the nucleic acid is distributed along the length of the membrane.

It is disclosed, e.g., in U.S. Pat. No. 7,067,287 that quartz filter paper may be used as the solid phase bondable to nucleic acids in methods for the recovery of nucleic acids under centrifugal forces or pressures and including particles. However, it is not found yet that quartz fiber filters are actually used in isolating/separating/purifying nucleic acids possibly it is not suitable for use in particle format and it is more well known for use in air sampling which is much different from isolating/separating/purifying nucleic acids. Another reason the quartz fiber filter is not been actually used in isolating/separating/purifying nucleic acids may be it is believed to be too dense to sorb nucleic acids.

Centrifugal force and pressure need instruments to generate the force and pressure and specific operation skills, and are thus undesirable, e.g., for places where expensive instruments and skilled persons are not affordable. In addition, centrifugal force and pressure may break down chains of nucleic acids into too short strings, resulting in that only nucleic acids of relatively small size could be obtained. Separating by distribution along the membrane may sometimes have concerns in qualities because both of nucleic acids and impurities together are spread out on the membrane.

Therefore, there is a need to develop a new method and apparatus for isolating nucleic acids.

BRIEF DESCRIPTION

In one aspect, a method is provided, comprising: sorbing a sample solution comprising nucleic acids to a sample receiving portion of a quartz fiber filter by contacting the sample solution with the sample receiving portion; and washing the sample receiving portion while keeping most of nucleic acids around the sample receiving portion by flowing a wash solution through the sample receiving portion under a wicking force directed away from the sample receiving portion.

In another aspect, an apparatus is provided. The apparatus comprises: a quartz fiber filter comprising: a sample receiving portion for sorbing a sample solution comprising nucleic acids by contacting with the sample solution and keeping most of nucleic acids around the sample receiving portion after a wash solution flowing therethrough under a wicking force directed away therefrom.

These and other advantages and features will be better understood from the following detailed description of preferred embodiments of the invention that is provided in connection with the accompanying drawings.

DETAILED DESCRIPTION

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

In the following specification and claims, the singular forms "a", "an" and "the" include plural referents, unless the context clearly dictates otherwise. Moreover, the suffix "(s)" as used herein is usually intended to include both the singular and the plural of the term that it modifies, thereby including one or more of that term.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. For example, in some circumstances, an event or capacity may be expected, while in other circumstances, the event or capacity maynot occur. This distinction is captured by the terms "may" and "may be".

Preferred embodiments of the present disclosure will be described hereinbelow with reference to the accompanying drawings. In the following description, well-known functions or constructions are not described in detail to avoid obscuring the disclosure in unnecessary detail.

Figure 1:
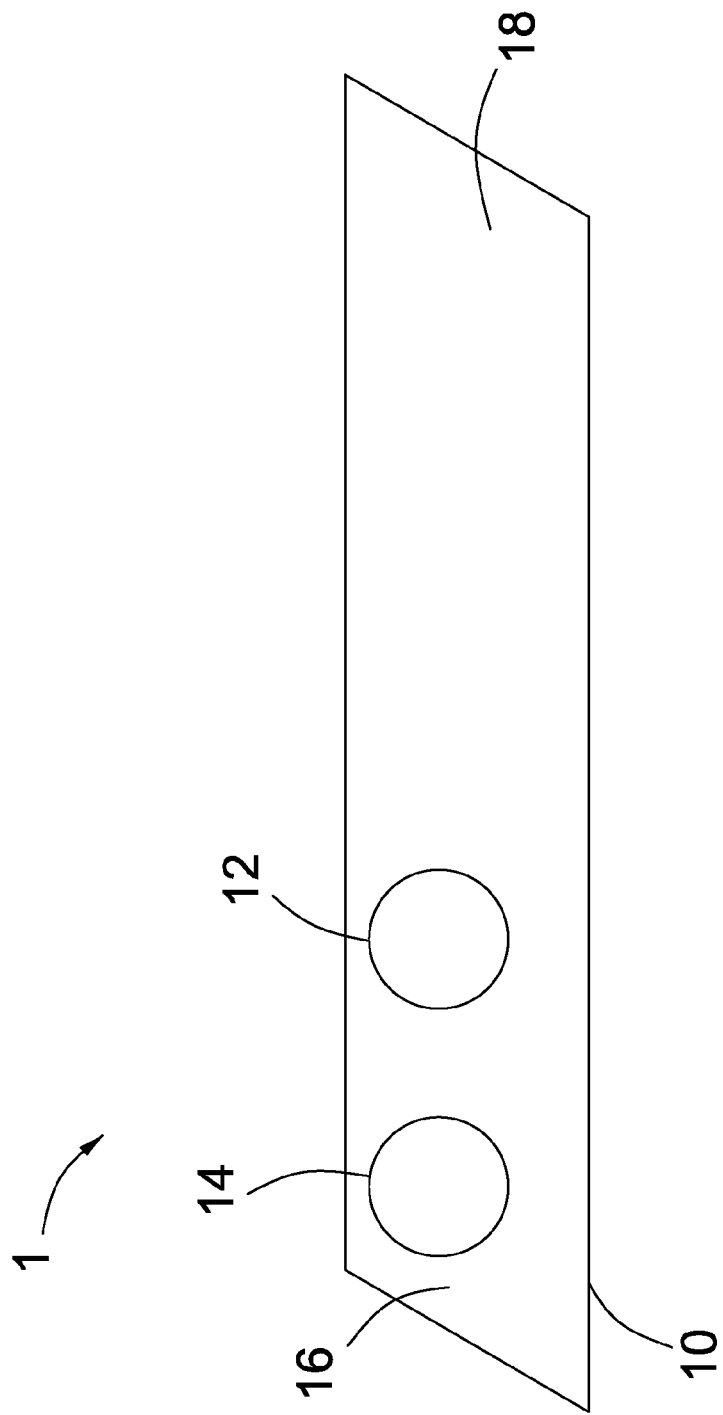
FIG. 1 is a schematic diagram of an apparatus in accordance with a first embodiment of the invention.

Please refer to FIG. 1, an apparatus 1 in accordance with a first embodiment of the present invention comprises: a quartz fiber filter 10 comprising: a sample receiving portion 12 for sorbing a sample solution (not shown) comprising nucleic acids (not shown) by contacting with the sample solution and keeping most of nucleic acids around the sample receiving portion after a wash solution (not shown) flowing therethrough under a wicking force (not shown) directed away from the sample receiving portion.

The quartz fiber filter 10 includes any porous and bibulous material to which the sample solution will sorb and which does not inhibit storage or subsequent analysis of the nucleic acid applied to the quartz fiber filter. In some embodiments, the quartz fiber filter 10 is made of pure quartz fibers with no binders. In some embodiments, the quartz fiber filter has a particle retention efficiency of about 98% for particles of a size of no less than 2.2 μm, a basis weight of 85 g/m$^2$, and a thickness in a range of from about 300 μm to about 600 μm. examples of quartz fiber filters suitable for this purpose include, but are not limited to, Whatman® grade QM-A quartz microfiber filters available from GE Healthcare Bio-Sciences Corp., New Jersey, USA), and AQFA quartz fiber filters available from Millipore Corporation, Billerica, Mass., USA.

The quartz fiber filter 10 may be in the form of an elongate strip, along which the wash solution applied thereon is able to travel. The quartz fiber filter 10 may be supported on a backing material such as a plastic material like polyester (Mylar®) or PET.

The apparatus may be a simple nucleic acid purification device, or alternatively may be a part or components of a whole nucleic acid analysis device/instrument.

The sample receiving portion 12 may be in any shape or configuration that the sample solution could be sorbed thereto. The sample receiving portion 12 may be either a section of the quartz fiber filter 10 itself or an absorbent pad, which is in liquid contact with the quartz fiber filter 10.

In some embodiments, the quartz fiber filter 10 may be an elongated strip comprising the sample receiving portion 12, a wash portion 14 distant from the sample receiving portion 12 for the wash solution (not shown) to be added thereto, a first end 16, and a second end 18. The wash portion 14 is located closer to the first end 16 than to the second end 18 and the sample receiving portion 12 is located closer to the second end 18 than the wash portion 14. In such an arrangement, when the wash solution is applied to the wash portion 14, most of the wash solution will flow from the wash portion 14 through the sample receiving portion 12 towards the second end 18 under a wicking force directed away from the sample receiving portion 12.

In some embodiments, the wash portion 14 is the first end 16 and the wash solution is applied to the quartz fiber filter by soaking the wash portion 14/16 in the wash solution while the sample receiving portion is located outside the surface of the wash solution.

As used herein, the term "sorb" means that the sample solution is absorbed, adsorbed or otherwise incorporated into or onto the sample receiving portion in such a way as not to be readily removed from the sample receiving portion unless subjected to conditions which are intentionally or inadvertently performed to remove the sorbed composition from the sample receiving portion.

The term "most of nucleic acids" used herein refers to a quantity of nucleic acids kept around the sample receiving portion, which may be at least about 15% of the total amount of nucleic acids in the sample solution sorbed to the sample receiving portion, at least 50% of the total amount of nucleic acids in the sample solution sorbed to the sample receiving portion, or at least 90% of the total amount of nucleic acids in the sample solution sorbed to the sample receiving portion.

The term "isolate, isolating or isolation" used herein indicates the act or action to separate or purify nucleic acids from a sample solution in a way to facilitate subsequent analysis/usage of nucleic acids such as amplification analyses.

As used herein, the phrase "nucleic acids" means either or both of deoxyribonucleic acids (DNA) and ribonucleic acids (RNA). Isolated nucleic acids may comprise single type of nucleic acids or 2 or more different types of nucleic acids. They may be single-stranded, double-stranded, linear or cyclic. Length of isolated nucleic acids is also not limited. It may be optional in a range from several by to several Mbp. It is however generally in a range from several by to several hundreds of kbp for ease of handling. The nucleic acid isolation/purification method of the present invention may swiftly recover a wider range of lengths of nucleic acids than a conventional method may. Length of nucleic acids isolated by the present invention may be in a range of from about 1 bp to about 1,500 kbp, preferably of from about 1 kbp to about 500 kbp, more preferably from about 20 kbp to about 200 kbp.

There is no limit to the analytes for the present invention. Examples of analytes include physiological/pathological body liquids (e.g., secretions, excretions, exudates and transudates) or cell suspensions (e.g., blood, lymph, synovial fluid, semen, saliva comprising buccal cells, skin scrapings, hair root cells, etc.) of humans and animals; physiological/pathological liquids or cell suspensions of plants; liquid products, extracts or suspensions of bacteria, fungi, plasmids, viruses etc.; liquid products, extracts or suspensions of parasites including helminths, protozoas, spirochetes, etc.; liquid extracts or homogenates of human or animal body tissues (e.g., bone, liver, kidney, etc.); media from DNA or RNA synthesis; mixtures of chemically or biochemically synthesized DNA or RNA; and any other source in which DNA and/or RNA is or may be in. In particular, analytes include physiological or clinical samples such as blood, blood cells and blood with anticoagulants. An exemplary method for removing an analyte from a source is removing a sample of nucleic acid in blood from a human or animal source by venipuncture.

The sample solution may be a solution comprising either or both of DNA and RNA, or, cells, cell components or cell extracts which comprise either or both of DNA and RNA, dissolved, suspended, mixed or otherwise contained therein. The sample solution may be a solution prepared from the analyte.

An exemplary method for preparing a sample solution comprising nucleic acids from an analyte includes the steps of: injecting a sample of analyte into a container; adding a nucleic acid-solubilizing reagent to the container, and mixing the sample with the nucleic acid-solubilizing reagent; incubating the resultant mixed solution; and adding a water-soluble organic solvent to the incubated mixed solution, in which the last two steps are optional. The nucleic acid-solubilizing reagent dissolves cell membranes and nuclear membranes to be dissolved, and solubilizes/disperses nucleic acids. Examples of the nucleic acid-solubilizing reagent include solutions comprising at least one of a chaotropic salt, a surfactant and a protease. The nucleic acid-solubilizing reagent may be fed in a dry state as well.

The method for preparing the sample solution comprising nucleic acids may be conducted with the aid of, for example, a ultrasonic wave treatment, a treatment using a sharp projection, or a high-speed stirring or vortexing treatment.

The preferable protease for the present invention is at least one of, e.g., serine, cystine and metallic proteases. Serine protease is not particularly limited and, for example, protease K may preferably be used. Cysteine protease is not particularly limited and, for example, papain and cathepsin may preferably be used. Metallic protease is not particularly limited and, for example, carboxypeptidase may preferably be used. A protease free of nuclease may be used. A protease comprising a stabilizer, such as metallic ions, may be used. More specifically, the magnesium ion in the form of magnesium chloride or the like, is preferable. A stabilizer may be incorporated at a concentration of about 1 to about 1000 mmol/mL, or preferably about 10 to about 100 mmol/mL of the total volume of the whole reaction system.

The protease may be used, upon addition, in an amount of preferably from about 0.001 IU to about 10 IU, more preferably from about 0.01 IU to about 1 IU, per ml of the whole reaction system.

A protease may be used together with a chaotropic salt, surfactant or another reagent. Alternatively, the protease may be used as a separate reagent from other reagents such as a chaotropic salt and a surfactant. In the latter case, a sample of analyte is first mixed with a reagent comprising a protease, and the mixture is then mixed with a reagent comprising a chaotropic salt and/or a surfactant. Or, the protease may be mixed after first mixing a sample of analyte with the reagent comprising a chaotropic acid and/or a surfactant.

The procedure for mixing a sample of analyte with a nucleic acid solubilizing reagent is not limited.

The yields of separated and purified nucleic acids may be increased by incubating the mixture of a sample of analyte and a nucleic acid-solubilizing reagent at a preferred temperature for a protease for a preferred reaction time. The incubation temperature is usually from about 20° C. to about 70° C., and the incubation time is usually from about 1 minute to about 90 minutes. The incubation method is not particularly limited, and may be conducted by dipping into a warm bath or a heating chamber.

The nucleic acid-solubilizing reagent solution has a pH in a range of preferably from about 5 to about 10, more from preferably about 6 to about 9, still more preferably from about 6.5 to about 8.

The concentration of a chaotropic salt in the nucleic acid-solubilizing reagent solution is preferably about 0.5 M or more, more preferably in a range from about 0.5 M to about 10 M, still more preferably in a range from about 5 M to about 8 M. Guanidine hydrochloride is a preferred chaotropic salt, but other chaotropic salts (e.g., sodium trifluoroacetate, sodium perchlorate, sodium iodide and guanidine thiocyanate) may also be used. Instead of a chaotropic salt, it is also possible to use urea as a chaotropic substance. These chaotropic substances may be used individually or in combination of two or more thereof.

The nucleic acid-solubilizing reagent solution may comprise a water-soluble organic solvent. As the water-soluble organic solvent, alcohols are preferred. The alcohols may be any of primary alcohols, secondary alcohols and tertiary alcohols. As the alcohol, methyl alcohol, ethyl alcohol, propyl alcohol and its isomers, and butyl alcohol and its isomers may preferably be used. These water-soluble organic solvents may be used independently or as a combination of two or more thereof. The concentration of the water-soluble organic solvent in the nucleic acid-solubilizing reagent solution is preferably in a range of from about 1% to about 20% by weight.

The concentration of the surfactant in the nucleic acid-solubilizing reagent solution is preferably in a range of from about 0.1% to about 20% by weight. Examples of the surfactant in the nucleic acid-solubilizing reagent solution include nonionic surfactants, cationic surfactants, anionic surfactants and amphoteric surfactants.

As the nonionic surfactant, polyoxyethylene alkylphenyl ether series surfactants, polyoxyethykene alkyl ether series surfactants, and fatty acid alkylamides may be used, with polyoxyethylene octyl phenyl ether (such as Triton™ X-100) and polyoxyethylene alkyl ether series surfactants being preferably usable. Polyoxyethylene alkyl ether series surfactants may be selected from among POE decyl ether, POE lauryl ether, POE tridecyl ether, POE alkylene decyl ether, POE sorbitan monolaurate, POE sorbitan monooleate, POE sorbitan monostearate, tetraoleic acid polyoxyethyolene sorbitol, POE alkylamine, and POE acetylene glycol.

Examples of cationic surfactants include cetyltrimethylammonium bromide, dodecyltrimethylammonium chloride, tetradecyltrimethylammonium chloride and cetylpyridinium chloride. These surfactants may be used independently or as a combination of two or more thereof.

In the case of recovering other nucleic acids than RNA, such as DNA, it is preferable to add an RNA-decomposing enzyme to a nucleic acid-solubilizing reagent solution to reduce the interference by RNA otherwise co-present in the recovered nucleic acids. It is also preferable to add DNA-decomposing enzyme inhibitor. RNA decomposing enzymes are not particularly limited, and enzymes capable of specifically decomposing RNA, such as ribonuclease H (RNase H), may preferably be used.

On the other hand, in the case of recovering other nucleic acids than DNA, such as RNA, it is preferable to add a DNA-decomposing enzyme to the nucleic acid-solubilizing reagent solution. Thus, interference by DNA otherwise co-present in the recovered nucleic acids may be reduced. It is also preferable to add RNA-decomposing enzyme inhibitor. As the RNA-decomposing enzyme inhibitor, those which specifically inhibit RNA-decomposing enzymes are preferred. DNA decomposing enzymes are not particularly limited, and enzymes capable of specifically decomposing DNA, such as DNase I may preferably be used.

In some embodiments, enzymes capable of specifically decomposing DNA or RNA may be added to the sample receiving portion after washing the quartz fiber filter with the wash solution.

The sample solution comprising nucleic acids may preferably comprise a defoaming agent. Examples of the defoaming agent include silicon-comprising defoaming agents (e.g., silicone oil, dimethylpolysiloxane, silicone emulsion, modified polysiloxane and silicone compound), alcohol series defoaming agents (e.g., acetylene glycol, heptanol, ethylhexanol, higher alcohol and polyoxyalkylene glycol), ether series defoaming agents (e.g., heptyl cellosolve and nonyl cellosolve-3-heptylsorbitol), fat-and-oil series defoaming agents (e.g., animal oils and plant oils), fatty acid series defoaming agents (e.g., stearic acid, oleic acid and palmitic acid), metallic soap series defoaming agents (e.g., aluminum stearate and calcium stearate), fatty acid ester series defoaming agents (e.g., natural wax and tributyl phosphate), phosphate series defoaming agents (e.g., sodium octylphosphate), amine series defoaming agents (e.g., diamylamine), amide series defoaming agents (e.g., stearic acid amide) and other defoaming agents (e.g., ferric sulfate and bauxite). Particularly preferably, a combination of a silicon-comprising defoaming agent and an alcohol series defoaming agent may be used as the defoaming agent.

An alcohol may preferably be used as a water-soluble organic solvent to be added to an incubated mixed solution. Any of a primary alcohol, a secondary alcohol and a tertiary alcohol may be used. Methyl alcohol, ethyl alcohol, propyl alcohol, butyl alcohol, and an isomer thereof may preferably be used. The concentration of such water-soluble organic solvent in the sample solution comprising nucleic acids is preferably in a range of from about 5% to about 90% by weight.

Both of the sample solution comprising nucleic acids and the wash solution may be applied to the quartz fiber filter by a tube, a pipette, or an automatic injector, or in any other applicable ways/tools. The wash solution flows along or through the quartz fiber filter under the wicking force and without external force and carries away impurities having a less affinity to the quartz fiber filter than nucleic acids, thereby washing the sample receiving portion while keeping most of the nucleic acids around the sample receiving portion.

The wash solution may be supplied to the quartz fiber filter at the same place as where the sample solution comprising nucleic acids is added, i.e., the sample receiving portion. The wash solution may also be applied to the quartz fiber filter at a place different from the sample receiving portion. In the former case, the sample receiving portion and the wash portion is the same place on the quartz fiber filter.

The wash solution may comprise an enzyme capable of degrading a contaminant, e.g., protein. Moreover, it may comprise deoxyribonuclease, ribonuclease or the like depending on circumstances. Use of a deoxyribonuclease-comprising wash solution will allow selective recovery of RNA. Similarly, use of a ribonuclease-comprising wash solution will allow selective recovery of DNA.

The wash solution preferably comprises a water-soluble organic solvent and/or water-soluble salt. The wash solution washes out an impurity in a sample solution, which is adsorbed on the quartz fiber filter together with nucleic acids. Therefore, it may have a composition which desorbs the impurity from the quartz fiber filter while keeping nucleic acids adsorbed. A water-soluble organic solvent, e.g., alcohol, in which nucleic acids are sparingly soluble, is suitable for desorbing components other than nucleic acid from the quartz fiber filter. At the same time, incorporation of a water-soluble salt enhances the effect of adsorbing nucleic acids to improve selective desorption of an unnecessary component.

The exemplary water-soluble organic solvents to be contained in a wash solution include methanol, ethanol, isopropanol, n-propanol, butanol and acetone, of which ethanol is more preferable. The water-soluble organic solvent is incorporated in a wash solution preferably at about 20% to about 100% by weight, more preferably about 40% to about 100% by weight.

On the other hand, the exemplary water-soluble salt to be contained in a wash solution is preferably a halide salt or tris(hydroxymethyl)aminomethane.

Figure 2:
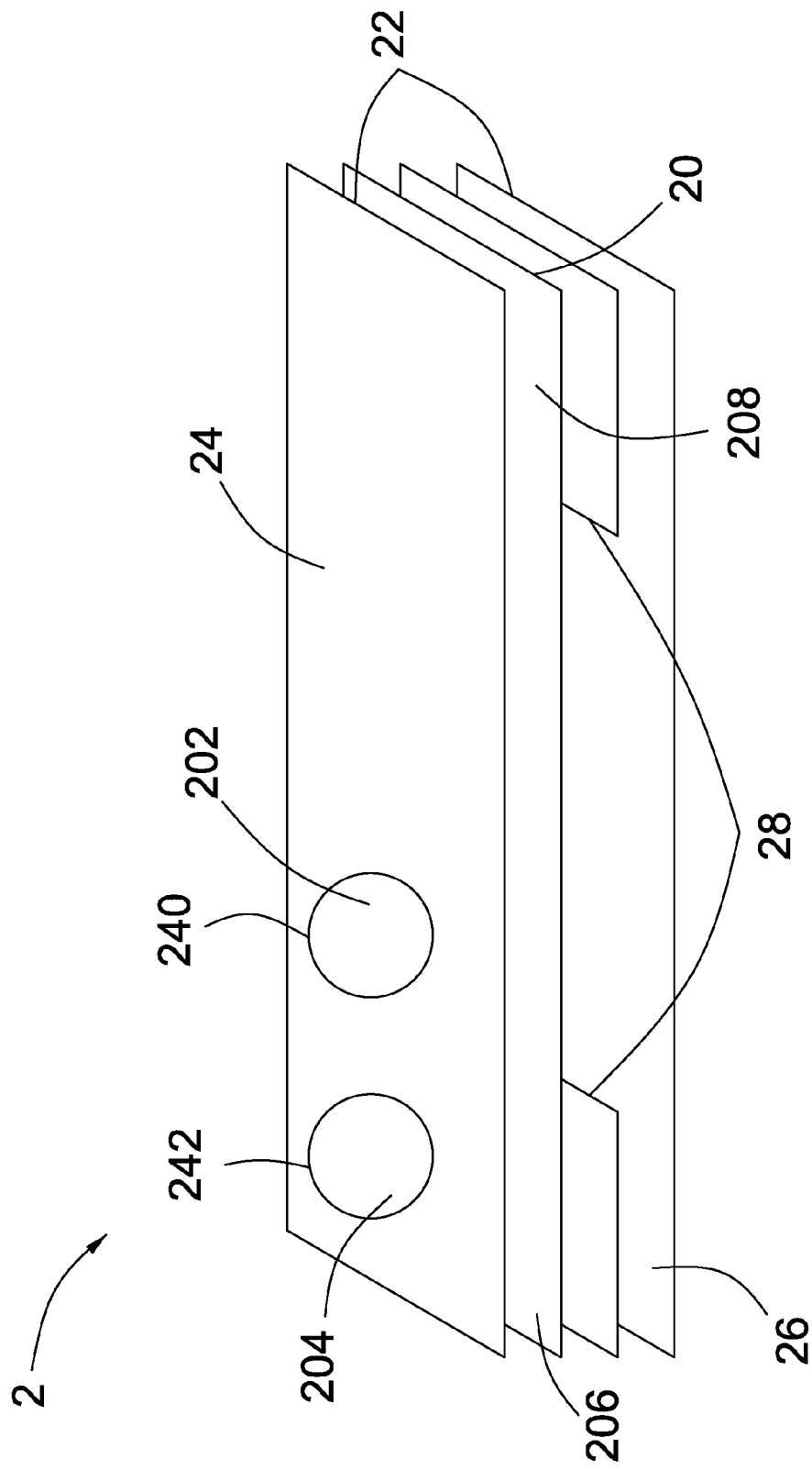
FIG. 2 is a schematic diagram of an apparatus in accordance with a second embodiment of the invention.

Referring to FIG. 2, an apparatus 2 in accordance with a second embodiment of the present invention comprises a quartz fiber filter 20, a plastic housing 22 comprising an upper half 24 and a lower half 26, and bibulous pads 28.

The quartz fiber filter 20 is similar with the quartz fiber filter 10 of the first embodiment and comprises a sample receiving portion 202 and a wash portion 204, a first end 206, and a second end 208. The wash portion 204 is located closer to the first end 206 than to the second end 208 and the sample receiving portion 202 is located closer to the second end 208 than the wash portion 204. In such an arrangement, when the wash solution is applied to the wash portion 204, more of the wash solution will flow from the wash portion 204 through the sample receiving portion 202 towards the second end 208 under a wicking force directed away from the sample receiving portion 202.

The plastic housing 22 encloses the quartz fiber filter 20 and the bibulous pads 28 therein. The upper and the lower halves 24, 26 may be molded integrally or separately. The upper half 24 comprises a sample opening 240 and a wash opening 242 corresponding in positions to the sample receiving portion 202 and the wash portion 204, respectively. While the sample solution comprising nucleic acids is added, the sample opening 240 may accommodate the sample solution comprising nucleic acids together with the sample receiving portion 202 before the sample solution comprising nucleic acids is completely sorbed.

The bibulous pads 28 are respectively adjacent to and vertically aligned with the wash portion 204 and the second end 208 to help to enhance the wicking force drawing the wash solution away from the sample receiving portion 202.

Figure 3:
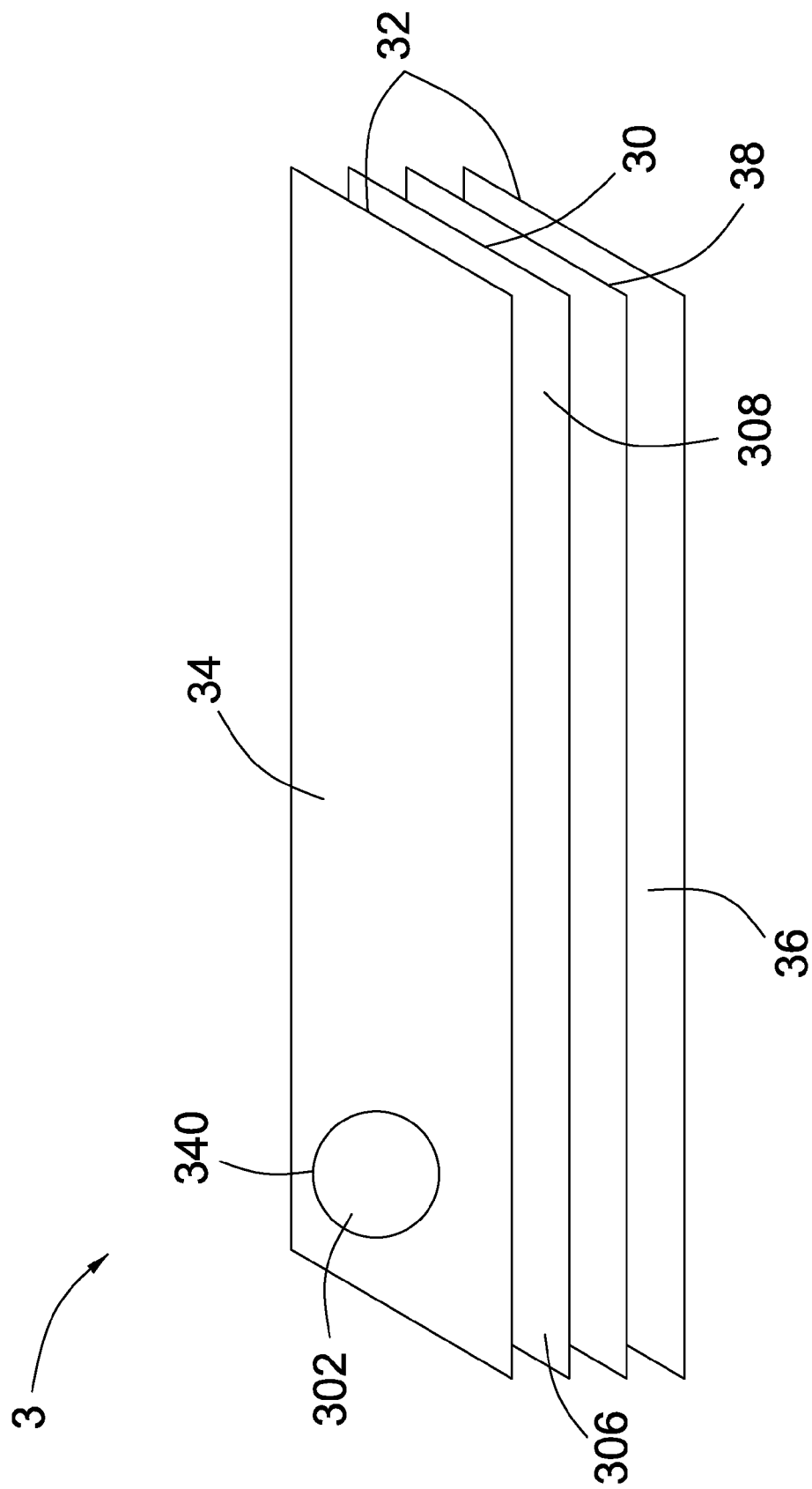
FIG. 3 is a schematic diagram of an apparatus in accordance with a third embodiment of the invention.

Please refer to FIG. 3, an apparatus 3 in accordance with a third embodiment of the present invention comprises a quartz fiber filter 30, a plastic housing 32 comprising an upper half 34 and a lower half 36, and a bibulous pad 38.

The quartz fiber filter 30 is similar with the quartz fiber filter 10 of the first embodiment and comprises a sample receiving portion 302, a first end 306, and a second end 308. The sample receiving portion 302 is located closer to the first end 306 than to the second end 308.

The plastic housing 32 encloses the quartz fiber filter 30 and the bibulous pad 38 therein. The upper and the lower halves 34, 36 may be molded integrally or separately. The upper half 34 comprises a sample opening 340 corresponding in position to the sample receiving portion 302. While the sample solution comprising nucleic acids is added, the sample opening 340 may accommodate the sample solution comprising nucleic acids together with the sample receiving portion 302 before the sample solution comprising nucleic acids is completely sorbed.

The bibulous pad 38 is adjacent to and vertically aligned with the quartz fiber filter 30 to help drawing the wash solution away from the sample receiving portion 302.

In such an arrangement, both the sample solution comprising nucleic acids and the wash solution are applied to the sample receiving portion 302 and when the wash solution is applied to the sample receiving portion 302, the wash solution will flow through the sample receiving portion 302 towards the second end 308 and/or the bibulous pad 38 under a wicking force directed away from the sample receiving portion 302.

The bibulous pad 28, 38 is made of bibulous material, such as cellulose, silica microfiber filter, glass fiber, and quartz fiber filter.

In some embodiments, the sample receiving portion may be located outside of the housing.

The method of the invention may comprise steps of: sorbing a sample solution comprising nucleic acids to a sample receiving portion of a quartz fiber filter by contacting the sample solution with the sample receiving portion; and washing the sample receiving portion while keeping most of nucleic acids around the sample receiving portion by flowing a wash solution through the sample receiving portion under a wicking force directed away from the sample receiving portion.

In the invention, the wicking force inherent from the porosity of the bibulous quartz fiber filter itself acts as the driving force to enable the wash solution to flow and carry away the impurities besides nucleic acids from the sample solution because of different affinities of impurities and nucleic acids to the porous quartz fiber filter, thereby eliminating the needs for instruments to generate the external driving force (e.g. centrifugation force and pressure) and personnel with specific skills and enabling isolation on site and in remote areas. It appears that by flowing the wash solution through the sample receiving portion to carry impurities away while keeping the nucleic acids around the sample receiving portion, the nucleic acids become sufficiently separated from other components in the sample solution to allow them to be detected using a conventional nucleic acid detection method such as PCR. In effect, this has a purification effect.

This method may be a highly cost effective and efficient method for conducting a simple purification step in any analysis, but in particular for an analysis which involves nucleic acid amplification such as the polymerase chain reaction (PCR) which may be conducted in the presence of the quartz fiber filter without any significant inhibition. The quartz fiber filter unexpectedly entraps nucleic acids after the sample solution comprising nucleic acids are applied thereto and after the wash solution flows therethrough to carry away impurities. Once separated on the quartz fiber filter, the nucleic acid may be subjected to further analysis in situ, or if necessary, nucleic acids may be eluted from or otherwise removed from the quartz fiber filter using a suitable buffer, and the analysis carried out on the eluate or extract.

After washing by the wash solution, the sample receiving portion usually changes back or close to back in color with respect to before the sample solution comprising nucleic acids is added. In some embodiments, the quartz fiber filter is dried at a temperature below 90° C. or preferably, at 37° C. or 40° C., or at the room temperature after washing and the quartz fiber filter, or more suitably the sample receiving portion of the quartz fiber filter, for example a small piece or punch extracted around the sample receiving portion is taken, for example in a laboratory environment, and utilised for further analysis.

For example, in order to detect the presence of a specific nucleic acid on the quartz fiber filter, the piece or punch is immersed into a PCR mixture. PCR mixtures may comprise reagents such as nucleotides, polymerase and a set of PCR primers that are designed to amplify a specific nucleic acid sequence, which may be characteristic of a particular organism. PCR mixtures may further comprise buffers, magnesium salts etc.

The Ct values obtained from the PCR analysis of nucleic acid on the quartz fiber filter were equivalent to those from analyses using conventional complex purification and/or storage methods. This suggests that the method and apparatus of the invention working to purify the nucleic acids and remove contaminants/inhibitors effectively.

As used herein, the nucleotides include a primer, (e.g., a PCR primer, a primer for reverse transcriptase initiated PCR), sets of oligonucleotide substrates for LCR, DNA or RNA probe, oligonucleotides used in genetic sequencing, or target sequence stabilizer.

As used herein, a "primer" means a fragment of oligonucleotides, which is capable of annealing to a complementary nucleic acid sequence on the quartz fiber filter, and which are oriented so that the primer will prime the synthesis of a strand of DNA (or conceivably, a strand of RNA) comprising a sequence complimentary to the other oligonucleotide. For some applications, it is desirable that the sequence of the oligonucleotide and its complimentary sequence are predetermined. In other applications, the sequence may be unknown. A plurality of degenerate primers or primers with sequences predicted to bind to the complementary sequence may be used. The primer-pair may be used to amplify a pair of complimentary sequences and the sequence between the two complimentary sequences of known or unknown size. In addition, the primer may be used to amplify a template that is initially double-stranded DNA or RNA, as well as single-stranded DNA or RNA. For a single-stranded template, it is understood that the sequence complementary to one of the oligonucleotides will be synthesized by elongation of the first primer as it is annealed to its complementary sequence.

Primers for PCR or for reverse transcriptase initiated PCR may be present as a primer-pair, as is usual, or there may be only one primer as may be the case with genomic-sequencing or some protocols for reverse transcriptase initiated PCR.

EXAMPLES

The following examples are included to provide additional guidance to those of ordinary skill in the art in practicing the claimed invention. Accordingly, these examples do not limit the invention as defined in the appended claims.

Example 1

Position Analysis after Isolation

A sample of human whole blood (2.5 µl) comprising an anticoagulant (sodium heparin), 0.25 µl of protease K (20 mg/ml) and 2.5 µl of a solution (66.87% guanidinium hydrochloride, and 4% Triton™ X-100) were added into a 1.5 ml microcentrifuge tube.

The microcentrifuge tube was shaken for approximately 15 seconds, then incubated at room temperature for about 10 minutes with intermittent vortexing to prepare the sample solution. At the end of the incubation, the color of the mixture in the microcentrifuge tube changed from red to dark brown.

After preparation, the obtained sample solution was transferred from the microcentrifuge tube through the sample opening of a plastic housing to contact with the sample receiving portion of the quartz fiber filter enclosed in the housing of an apparatus configured as shown in FIG. 2. The quartz fiber filter was a 4 mm-width×6 cm-length strip of Whatman® grade QM-A quartz microfiber filter obtained from GE Healthcare Bio-Sciences Corp., New Jersey, USA. The plastic housing was A-9 plastic housing obtained from Shanghai Jieyi Biotechnology Co., Ltd., Shanghai, China.

The bibulous pads below the wash portion and the second end were Whatman® grade 470 special purpose filter papers obtained from GE Healthcare Bio-Sciences Corp., New Jersey, USA.

After about 5 seconds since the transfer, the sample solution was observed to have been absorbed to the sample receiving portion of the quartz fiber filter and the sample receiving portion's color turned to brown. A wash solution (150 μl, 80% ethanol solution) was then added through the wash opening of the housing to wash the sample receiving portion by allowing the wash solution to flow from the wash portion in communication with the wash opening through the sample receiving portion.

When no visible impurities were observed around the sample receiving portion and the sample receiving portion's color turned back into the color before the sample solution was added, the apparatus was put in an oven at 37° C. for 30 minutes for drying. From the sample solution was added to the sample receiving portion's color turned back, it only took about 5 minutes. After drying, the quartz fiber filter was taken out of the housing and was cut into 12 small pieces along the length thereof each having a width of 4 mm and a length of 5 mm Each small piece was placed into a separate sample well of 0.8% agarose gel to conduct the pulsed field gel electrophoresis.

The pulsed field gel electrophoresis was carried out on a CHEF Mapper® XA system from Bio-Rad Laboratories, Inc., California, U.S.A., with a voltage of 120 V for 45 minutes. After electrophoresis, the agarose gel was stained by 1×SYBR Green I solution for 1.5 hours and then scanned using a Typhoon™ Trio™ variable mode imager, GE Healthcare Bio-Sciences Corp., New Jersey, USA to obtain the electrophoresis image.

Figure 4:
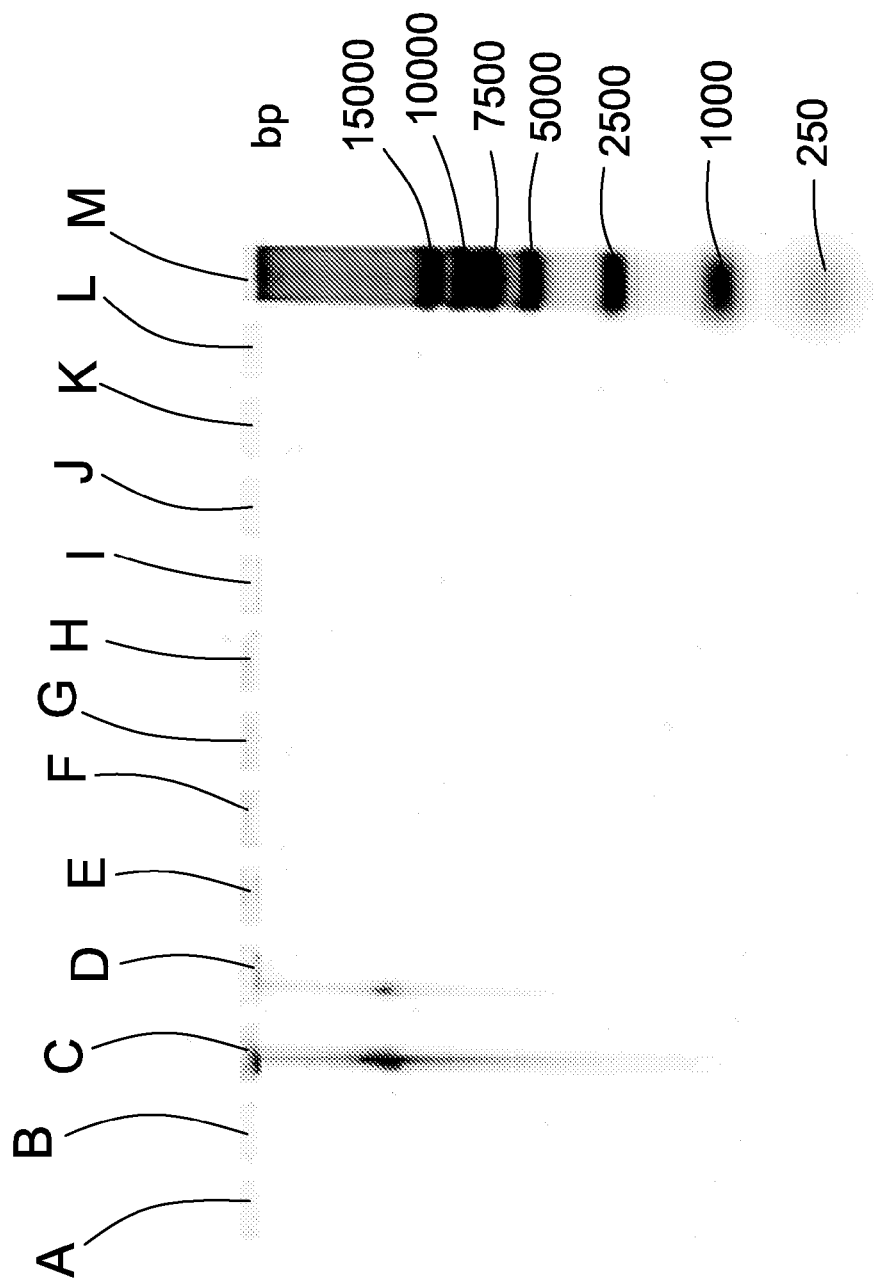
FIG. 4 is an electrophoresis image obtained in example 1.

The electrophoresis image is shown in FIG. 4. Lanes A-L in FIG. 4 represent images of pieces from the first end to the second end of the strip in sequence, e.g., lanes A-B represent images of pieces corresponding to the first end and the wash portion, lanes C-D represent images of pieces corresponding to the sample receiving portion, and lane M stands for the image of the DNA marker (DL 15,000, Takara). The image shows that after washing, most of nucleic acids were kept around the sample receiving portion.

Example 2

Size Analysis after Isolation

A quartz fiber filter strip similar with the one used in example 1 was contacted with the same amount of a sample solution prepared in the same way as in example 1 and washed with a wash solution the same as that in example 1 in the same way as in example 1.

Figure 5:
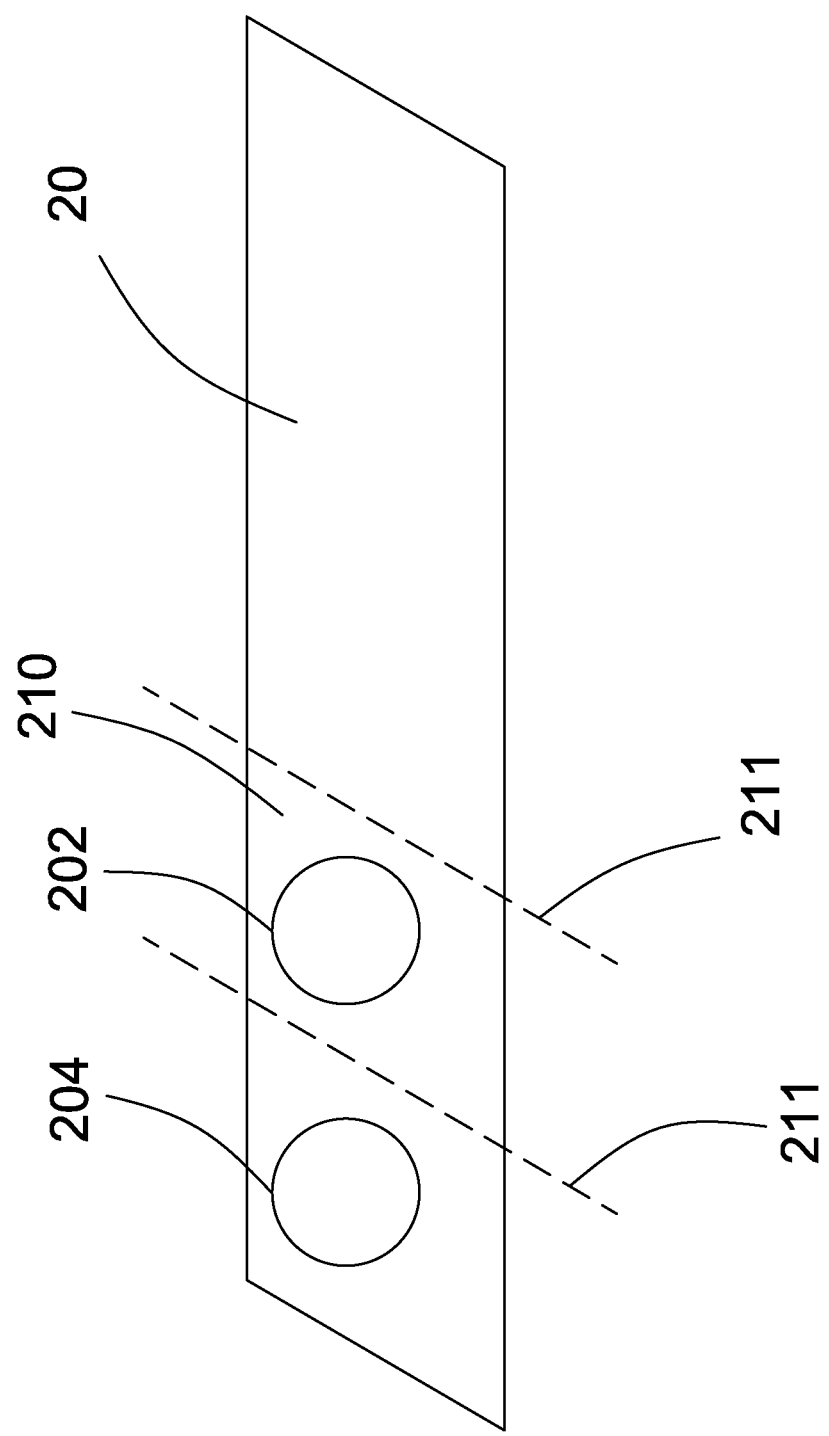
FIG. 5 is a schematic diagram showing that how a piece was taken for electrophoresis in example 2.

Once the quartz fiber filter strip was dried in the same way as in example 1, the quartz fiber filter was taken out of the plastic housing and a piece 210 (1 cm in length) around the sample receiving portion 202 between dotted lines 211 was cut from the quartz fiber filter strip 20 as is shown in FIG. 5. The 1 cm-length piece 210 was then cut in half, and the two halves were placed in a sample well of a 1% agarose gel to conduct the pulsed field gel electrophoresis.

Figure 6:
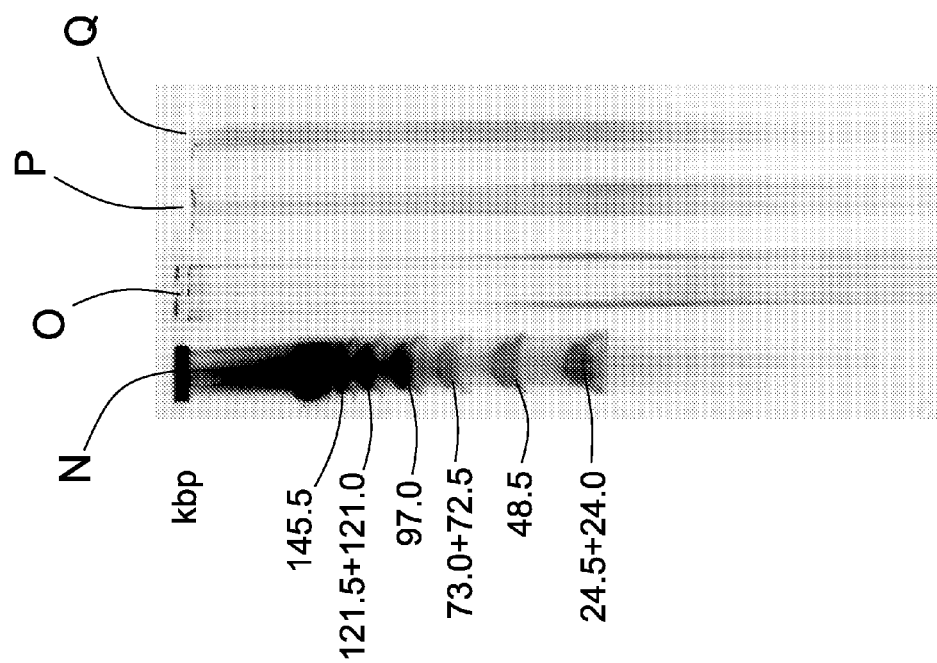
FIG. 6 is an electrophoresis image obtained in example 2 and comparative example 1.

Pulsed field gel electrophoresis was carried out on the CHEF Mapper® XA system, with a voltage of 6 v/cm at a temperature of 10° C. for 24 hours. After electrophoresis, the agarose gel was stained by 1×SYBR Green I solution for 5 hours and then scanned using the Typhoon™ Trio™ variable mode imager to obtain the electrophoresis image. The pulsed field gel electrophoresis image is shown in FIG. 6.

Comparative Example 1

DNA solution (2.5 μl) extracted from 2.5 μl of human whole blood comprising sodium heparin (anticoagulant) using QIAamp blood mini kit (QIAGEN) following operation protocols recommended in the product brochure was mixed with 2.5 μl of water and was placed in a sample well of a 1% agarose gel to conduct electrophoresis in the same way as in example 2.

Another 2.5 μl of DNA solution extracted from 2.5 μl of human whole blood comprising sodium heparin (anticoagulant) using QIAamp blood mini kit (QIAGEN) following operation protocols recommended in the product brochure was mixed with 2.5 μl water and was dropped on a strip the same as that used in example 1. After drying, a 1 cm-length piece of quartz fiber filter was cut around the sample receiving portion and placed into a separate sample well of a 1% agarose gel to conduct electrophoresis in the same way as in example 2.

Pulsed field gel electrophoresis images are also shown in FIG. 6. In FIG. 6, lane N represents MidRange II PFG marker, lane O is the image of the mixture of 2.5 μl DNA and 2.5 μl water of comparative example 1, lane P is the image of the piece of comparative example 1 and lane Q is the image of the piece of example 2.

As can be seen from FIG. 6 that the size range of DNA isolated/purified in comparative example 1 matches the product introduction mentioning that the size of DNA extracted by QIAGEN blood mini kit is from 200 bp to 50 kbp, and is much narrower than the size range of DNA isolated/purified in example 2.

Example 3

Amount Analysis after Isolation

Three strips of quartz fiber filter similar with the one used in example 1 were respectively contacted with the same amount of three sample solutions respectively prepared in the same way as in example 1 and respectively washed with three wash solution the same as that in example 1 in the same way as in example 1.

After drying in the same way as in previous examples, a 1.2 mm-diameter piece was punched around the sample receiving portion by a Harris Uni-core 1.2 mm puncher from each strip. Each of the pieces was placed into a 25 μl PCR tube containing 25 μl master-mix for Taqman real-time PCR for beta-actin (1×PCR buffer containing Ex Taq HS, 300 nM each beta-actin primer and 100 nM beta-actin probe).

Comparative Example 2

Three samples of 2.5 μl of DNA solution each extracted from 2.5 μl of human whole blood comprising anticoagulant (sodium heparin) using QIAamp blood mini kit (QIAGEN) following operation protocols recommended in the product brochure was each mixed with 2.5 μl water and was each dropped on a quartz fiber filter strip the same as that used in example 1. After drying, a 1.2 mm-diameter piece was punched at the sample receiving portion by a Harris Uni-core 1.2 mm puncher from each strip. Each piece was placed into a 25 μl PCR tube containing 25 μl master-mix for Taqman real-time PCR for beta-actin (1×PCR buffer containing Ex Taq HS, 300 nM each beta-actin primer and 100 nM beta-actin probe).

Real-time PCR was carried out on a Smart Cycler® II thermocycler (Cepheid), with cycling conditions of 30 seconds at 95° C., and then followed by 40 2-step cycles of 5 seconds at 95° C. and 20 seconds at 60° C.

Beta-actin was successfully amplified using pieces of example 3 and comparative example 2. The Ct values are shown in Table 1. The result shows that the DNA purified in example 3 has comparable/better amount as in comparative example 2.

TABLE 1

|  | Ct values |
| --- | --- |
| pieces from comparative example 2 | 29.41, 30.06, 29.49 |
| pieces from example 3 | 29.23, 29.39, 29.23 |

Example 4

Isolation without Plastic Housing

The same amount of a sample solution prepared in the same way as in example 1 was contacted with a sample receiving portion of a strip the same as the one used in example 1. After about 5 seconds, the sample solution was observed to have been absorbed to the strip and the sample receiving portion's color turned to brown.

Figure 7:
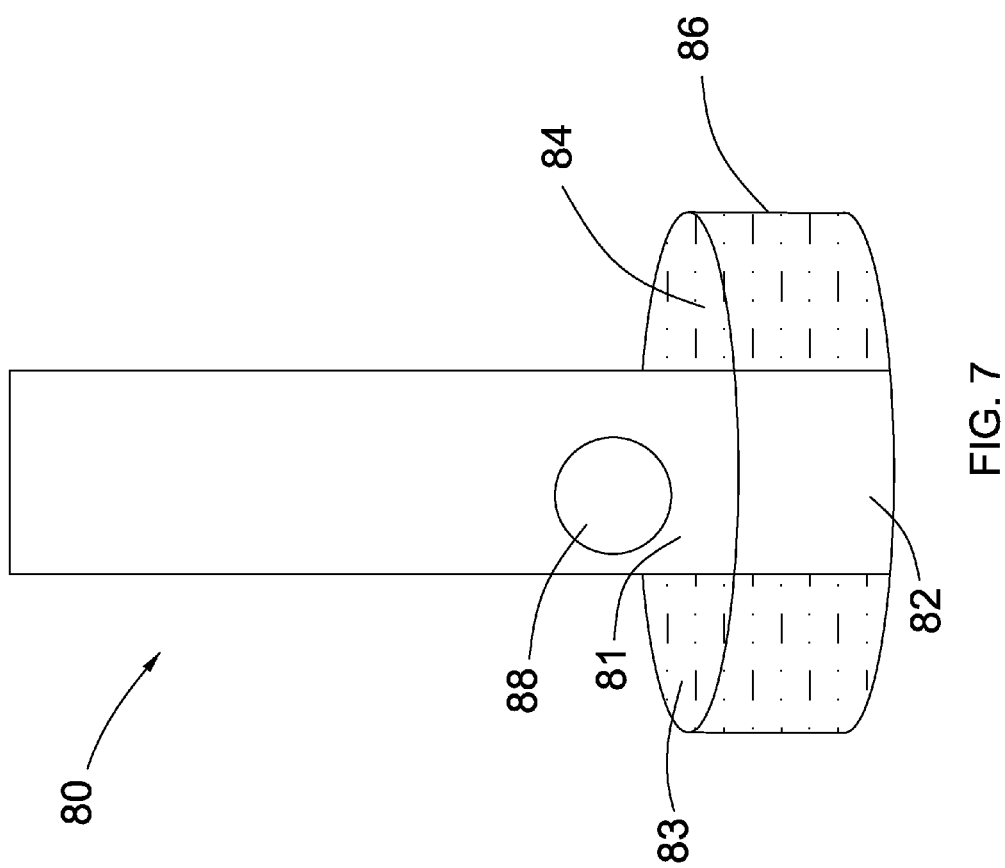
FIG. 7 is a schematic diagram showing the washing step of example 5.

Immediately, as is shown in FIG. 7, the first end 82 of the strip 80 was soaked in 150 µl of wash solution 84 the same as that in example 1 in a well 86 of a 96-well plate with the sample receiving portion 88 and the portion 81 between the sample receiving portion 88 and the wash solution surface 83 was not soaked in the wash solution 84. After about 5 minutes, the sample receiving portion's color turned back, the strip was taken out of the well 86 and dried in a 37° C. oven for 20 minutes.

A 1.2 mm-diameter piece was punched and amplified in the same system as in example 3.

The experiment was repeated once. Beta-actin gene was successfully amplified using each of the two pieces and the Ct values were 27.99 and 28.08.

Comparative Example 3

Isolation without Drying

A quartz fiber filter strip the same as the one used in example 1 was contacted with the same amount of a sample solution prepared in the same way as in example 1 and washed with the wash solution the same as that in example 1 in the same way as in example 1.

Without any drying step, a 1.2 mm-diameter piece was immediately punched after washing and amplified in the same system as in example 4. Beta-actin gene could not be successfully amplified using this piece.

Example 5

Isolation Using a Single Import

An apparatus configured as shown in FIG. 3 was used. A prepared sample solution similar as that of example 1 was dropped through the sample opening of the plastic housing to contact with the sample receiving portion of a quartz fiber filter strip the same as the one used in example 1.

After about 5 seconds, the sample solution was observed to have been absorbed to the sample receiving portion of the quartz fiber filter strip and the sample receiving portion's color turned to brown. A wash solution (150 µl, 80% ethanol solution) was then added through the sample opening of the housing to wash the sample receiving portion.

After drying in the same way as in previous examples, a 1.2 mm-diameter piece was punched at the sample receiving portion by a Harris Uni-core 1.2 mm puncher from the solid strip and amplified in the same system as in example 4.

The experiment was repeated once. Beta-actin gene could be successfully amplified using both of the pieces and the Ct values of the amplification were 27.76 and 28.73.

Example 6

Comparative Analysis with Un-Washed Strip

The same amount of a sample solution prepared in the same way as in example 1 was added to a strip the same as the one in example 1. After drying, a 1.2 mm-diameter piece was punched and amplified in the same way as in example 4.

The same amount of a sample solution prepared in the same way as in example 1 was added to a strip the same as the one in example 1 before the strip was washed and dried in the same way as in example 1. A 1.2 mm-diameter piece was also punched and amplified as in example 4 for comparison.

Beta-actin gene could be amplified using the both pieces. Ct values are shown in Table 2 below. The Ct value of un-washed piece was much bigger than the washed piece. That is to say, after washing, higher DNA amplification efficiency was obtained.

TABLE 2

|  | Ct value (2 replicates) |
| --- | --- |
| pieces without washing | 38.93, 36.89 |
| pieces with washing | 29.59, 28.22 |

Example 7

Comparative Analysis with the Human Whole Blood Sample

Human whole blood (2.5 µl) comprising sodium heparin (anticoagulant) was mixed with 2.5 µl of water and was dropped onto a sample receiving portion of a strip the same as the one in example 1. After drying, a 1.2 mm-diameter piece centered with the sample receiving portion was punched and amplified in the same way as in example 4.

A 1.2 mm-diameter piece was also punched in the same way as example 4 from a strip the same as the one used in example 1 added with the same amount of the sample solution in the same way as in example 1, washed with the same amount of the wash solution in the same way as in example 1 and dried in the same way as in example 1 to be amplified in the same way as example 4 for comparison.

Each experiment was repeated once. Beta-actin gene was amplified using the four pieces. Ct values are shown in Table 3. The Ct values of the pieces without washing were much bigger than the pieces with washing. That is to say, without nucleic-acid solubilizing reagent etc. in preparing the sample solution, amplification still worked, but after washing, a higher DNA amplification efficiency was obtained.

TABLE 3

|  | Ct value (2 replicates) |
| --- | --- |
| pieces with washing | 29.36, 28.48 |
| pieces without washing | 32.42, 32.44 |

Example 8

Comparative Analysis with Commercially Available Prototype

A sample solution was prepared in the same way as in example 1 using 2.5 µl of human whole blood comprising sodium heparin (anticoagulant), 0.25 µl of protease K (20 mg/ml) and 5 µl of a solution (66.87% guanidinium chloride, and 4% Triton™ X-100). The sample solution was added to a strip the same as the one used in example 1. After the sample solution was observed to have been sorbed, 400 µl of wash solution the same as the one used in example 1 was added to the wash portion to wash the sample receiving portion for 5 minutes.

A sample solution was prepared in the same way as in example 1 using 2.5 µl of human whole blood comprising sodium heparin (anticoagulant) and 5 µl of lysis solution from a Punch-it™ NA-sample kit obtained from Nanohelix Co., Ltd., Daejeon, South Korea was added to the sample receiving portion of the Punch-it™ NA-sample kit. After the sample solution was observed to have been sorbed, 400 µl of wash solution of the Punch-it™ NA-sample kit was added to the wash portion to wash the sample receiving portion for 5 minutes.

After drying in the same way as in previous examples, it was observed that the sample receiving portion of the Punch-it™ NA-sample kit still had color different from the color before the sample solution was added but the sample receiving portion of the strip was changed back.

The experiment was repeated. Two pieces were respectively punched from the Punch-it™ NA-sample kits and the strips and amplified in the same way as in previous examples. Ct values of the two pieces from the Punch-it™ NA-sample kits were 31.35 and 32.13, higher than those of the strips, 28.20 and 27.78.

While the disclosure has been illustrated and described in typical embodiments, it is not intended to be limited to the details shown, since various modifications and substitutions may be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A method for isolating nucleic acids comprising:
   sorbing a sample solution comprising nucleic acids to a sample receiving portion of a quartz fiber filter by contacting the sample solution with the sample receiving portion; and
   washing the sample receiving portion while keeping most of nucleic acids around the sample receiving portion by flowing a wash solution through the sample receiving portion under a wicking force directed away from the sample receiving portion, wherein the quartz fiber filter has a particle retention efficiency of about 98% for particles of a size of no less than 2.2 µm, a basis weight of 85 g/m$^2$, and a thickness in a range of from about 300 µm to about 600 µm.

2. The method of claim 1, wherein the sample solution comprises a chaotropic salt.

3. The method of claim 2, wherein the wash solution comprises at least one of ethanol and isopropanol.

4. The method of claim 1, wherein the quartz fiber filter comprises a wash portion distant from the sample receiving portion and the wash solution is added to the wash portion.

5. The method of claim 4, wherein the quartz fiber filter is an elongated strip comprising a first end, the wash portion, the sample receiving portion, and a second end, the wash portion is located closer to the first end than to the second end and the sample receiving portion is located closer to the second end than the wash portion.

6. The method of claim 5, further comprising: providing a bibulous pad made of at least one of cellulose, silica microfiber filter, glass fiber, and quartz filter, and adjacent to and vertically aligned with at least one of the wash portion and the second end.

7. The method of claim 5, wherein the wash portion is the first end and is soaked in the wash solution while the sample receiving portion is located outside the surface of the wash solution in the step of washing.

8. The method of claim 1, further comprising: providing a bibulous pad made of at least one of cellulose, silica microfiber filter, glass fiber, and quartz filter, and adjacent to and vertically aligned with the quartz fiber filter, wherein the wash solution is added to the sample receiving portion.

9. The method of claim 1, further comprising: drying the quartz fiber filter after washing.

* * * * *

UNITED STATES PATENT AND TRADEMARK OFFICE
CERTIFICATE OF CORRECTION

| | | |
|---|---|---|
| PATENT NO. | : 9,441,220 B2 | Page 1 of 1 |
| APPLICATION NO. | : 14/364436 | |
| DATED | : September 13, 2016 | |
| INVENTOR(S) | : Lin Chen et al. | |

It is certified that error appears in the above-identified patent and that said Letters Patent is hereby corrected as shown below:

On the Title Page

At (72) Inventors, after (CN): delete "Bing Shang" and insert --Bing Zhang--.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*